(12) United States Patent
Miller et al.

(10) Patent No.: US 8,434,475 B2
(45) Date of Patent: May 7, 2013

(54) NITRIC OXIDE REACTOR AND DISTRIBUTOR APPARATUS AND METHOD

(75) Inventors: Randy J. Miller, Orem, UT (US); Christie M. Jones, Chula Vista, CA (US)

(73) Assignee: Genosys, Inc., Provo, UT (US)

( * ) Notice: Subject to any disclaimer, the term of this patent is extended or adjusted under 35 U.S.C. 154(b) by 942 days.

(21) Appl. No.: 12/361,151

(22) Filed: Jan. 28, 2009

(65) Prior Publication Data
US 2010/0018526 A1 Jan. 28, 2010

Related U.S. Application Data

(60) Provisional application No. 61/025,230, filed on Jan. 31, 2008.

(51) Int. Cl.
*A61M 15/00* (2006.01)
*A61M 16/00* (2006.01)

(52) U.S. Cl.
USPC ............ 128/203.12; 128/202.26; 128/203.25; 424/718

(58) Field of Classification Search .................. 424/718; 128/202.26, 203.12, 203.25
See application file for complete search history.

(56) References Cited

U.S. PATENT DOCUMENTS

| | | |
|---|---|---|
| 5,427,797 A | 6/1995 | Frostell et al. |
| 5,713,349 A | 2/1998 | Keaney |
| 5,823,180 A | 10/1998 | Zapol |
| 5,839,433 A | 11/1998 | Higgenbottam |
| 5,873,359 A | 2/1999 | Zapol |
| 6,000,403 A | 12/1999 | Cantwell |
| 6,019,100 A | 2/2000 | Alving et al. |
| 6,063,407 A | 5/2000 | Zapol et al. |
| 6,131,572 A | 10/2000 | Heinonen |
| 6,142,147 A | 11/2000 | Head et al. |
| 6,149,606 A | 11/2000 | Alving et al. |
| 6,432,077 B1 | 8/2002 | Stenzler |
| 6,458,109 B1 | 10/2002 | Henley et al. |
| 6,572,594 B2 | 6/2003 | Satterfield et al. |
| 6,581,599 B1 | 6/2003 | Stenzler |
| 6,601,580 B1 | 8/2003 | Bloch et al. |
| 6,612,306 B1 | 9/2003 | Mault |
| 6,670,323 B1 | 12/2003 | Looker et al. |
| 6,763,832 B1 * | 7/2004 | Kirsch et al. ............. 128/207.18 |
| 6,786,217 B2 | 9/2004 | Stenzler |
| 6,793,644 B2 | 9/2004 | Stenzler |
| 7,017,573 B1 | 3/2006 | Rasor et al. |
| 7,045,152 B2 | 5/2006 | Stamler |
| 7,122,018 B2 | 10/2006 | Stenzler et al. |

(Continued)

FOREIGN PATENT DOCUMENTS

| | | |
|---|---|---|
| WO | 2006/110923 | 10/2006 |
| WO | 2007/057763 | 5/2007 |

*Primary Examiner* — Lynne Anderson
*Assistant Examiner* — Bradley Philips
(74) *Attorney, Agent, or Firm* — Pate Baird, PLLC

(57) ABSTRACT

A reaction and distribution system may include a distributor securable near or in a path correspond to a breathing passage such as the nostrils or the mouth of a user for delivering nitric oxide therapy thereto. The distributor may contain an internal reactor for creating the nitric oxide from reactants. Alternative embodiments may rely on a line delivering nitric oxide to the distributor from a remote generator such as a cannister carried in a pocket or placed/at the bedside of a user.

10 Claims, 5 Drawing Sheets

U.S. PATENT DOCUMENTS

| | | | |
|---|---|---|---|
| 7,914,743 B2 * | 3/2011 | Fine et al. | 422/120 |
| 2004/0197274 A1 * | 10/2004 | Fein et al. | 424/45 |
| 2006/0172018 A1 * | 8/2006 | Fine et al. | 424/718 |
| 2007/0190184 A1 * | 8/2007 | Montgomery et al. | 424/718 |
| 2010/0104667 A1 * | 4/2010 | Fine et al. | 424/718 |
| 2011/0240020 A1 * | 10/2011 | Fine et al. | 128/202.26 |

* cited by examiner

NITRIC OXIDE REACTOR AND DISTRIBUTOR APPARATUS AND METHOD

RELATED APPLICATIONS

This application claims the benefit of U.S. Provisional Patent Application Ser. No. 61/025,230, filed on Jan. 31, 2008.

BACKGROUND

1. The Field of the Invention

This invention relates to treatments providing nitric oxide as a vasodilator, and, more particularly, to generation and delivery of gaseous nitric oxide for inhaling.

2. Background

The discovery of the nitric oxide effect in live tissues garnered a Nobel prize. Much of the work in determining the mechanisms for implementing and the effects of nitric oxide administration are reported in literature including papers, advertising, catalogs, and patents. Much of the work deals with introduction of substances that provide a nitric oxide effect in the body. Still other applications may involve topical preparations introducing nitric oxide. Still other applications rely on bottled nitric oxide gas. Introduction of nitric oxide to the human body has traditionally been expensive.

The therapies, compositions, and preparations are sufficiently expensive to inhibit more widespread use of such therapies. What is needed is a comparatively inexpensive mechanism for introducing nitric oxide in a single dosage over a predetermined period of time. Also, what is needed is a simple introduction method for providing nitric oxide suitable for inhaling.

BRIEF SUMMARY OF THE INVENTION

In accordance with the foregoing, certain embodiments of an apparatus and method in accordance with the invention provide a reactive kit having two compounds, typically disposed in carriers. The two compounds are separated from one another prior to administration. In order to administer the nitric oxide, reactants are mixed in with one another beginning a reaction releasing nitric oxide.

An adhesive member may secure a distributor to a mask or directly to the skin of a user proximate the nose. Nitric oxide may thus be introduced into the breathing air of a subject. Nitric oxide amounts may be engineered to deliver at a comparatively low rate in the hundreds of parts per million, or in a therapeutically effective amount on the order of thousands of parts per million. For example, sufficient nitric oxide may be presented through nasal inhalation to provide approximately five thousand parts per million in breathing air. This may be diluted due to additional bypass breathing through nasal inhalation or through oral inhalation.

One embodiment of an apparatus and method in accordance with the present invention may rely on a small reactor feeding a distributor secured to an upper lip of a user. A diffuser may secure to one side of an adhesive strip, while a treated backing paper, easily removable, may be secured to the opposite side of the adhesive strip. A reactor may be sized to contain reactants as solids, liquids, or gels compounded to have an appropriate moisture content to support reaction of reactants. A second reactant composition in a carrier may be sealed or otherwise separated from the first reactant composition. For example, the two reactants may be contained in separate volumes. Alternatively, reactive solids may simply be appropriately combined dry, or even separated by an intervening layer, such as a film, paper, or the like. The reaction may begin upon introduction of a liquid transport material to support ionic or other chemical reactions. The reactants held in separate, sealed volumes may be opened and mixed or otherwise placed in contact with one another to permit combination of the ingredients needed to form nitric oxide. In one embodiment, the reactants may include an acid, such as ascorbic acid, citric acid, or the like as a hydrogen donor. The other reactant may include potassium nitrite, sodium nitrite or the like.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
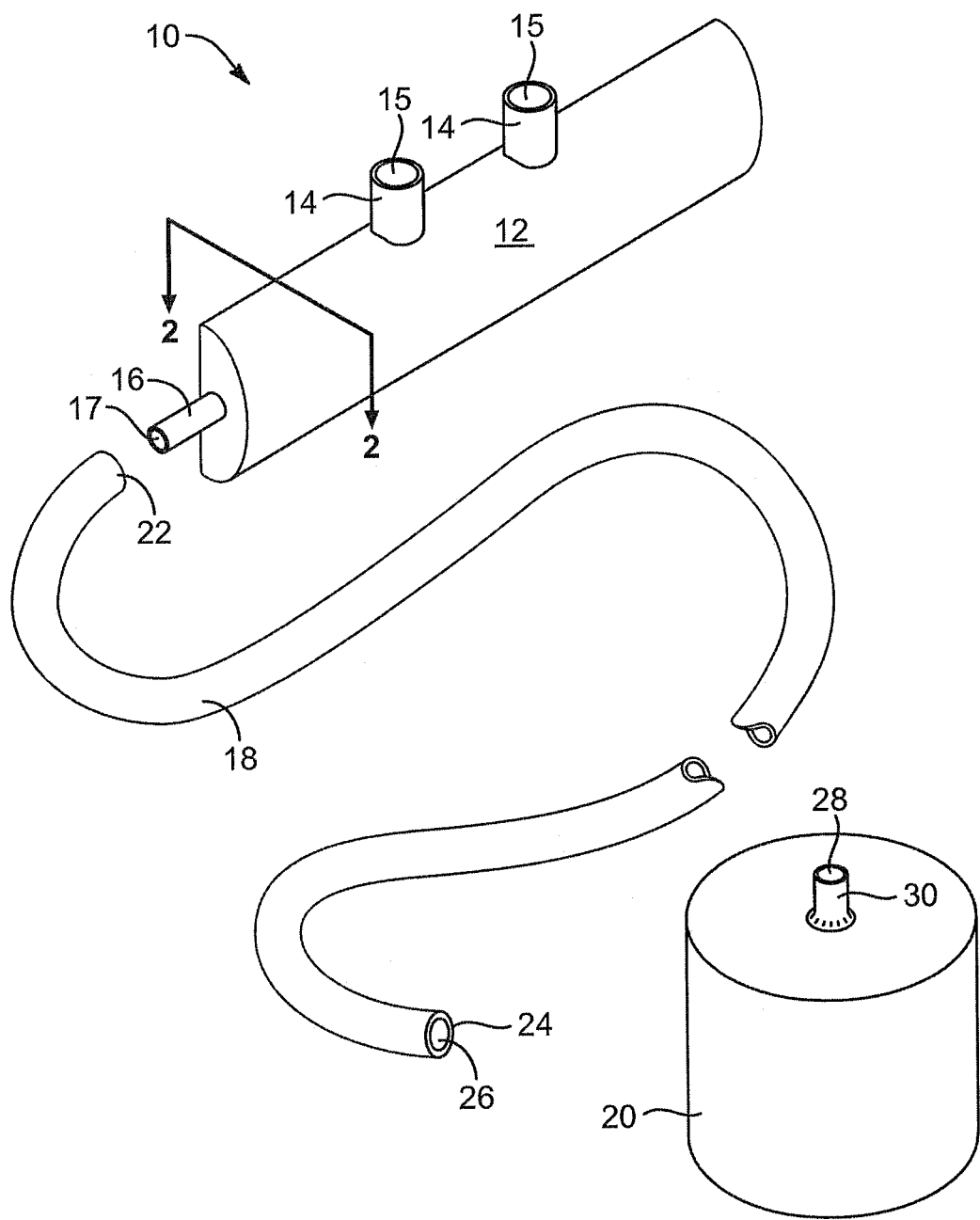
FIG. 1 is a perspective view of one embodiment of a system for generating and delivering nitric oxide in accordance with the invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, an apparatus 10 in accordance with the invention may include a vessel 12 or distributor 12. The distributor 12 may be configured to be flexible or may be pre-formed to fit the anatomy of a user. Typically, the distributor 12 will be placed on the upper lip of a user to provide the outputs 14 (e.g., output ports 14, or simply ports 14) access to the nostrils of a user during breathing. Each of the outputs 14 has an opening 15 for delivering nitric oxide directly into the nostrils of a user. Typically, sufficient clearance provides a bypass for air in addition to the nitric oxide from the distributor 12.

In certain embodiments of an apparatus in accordance with the invention, a distributor 12 may include a port 16 to operate as an input 16 for receiving nitric oxide from another source. For example, the port 16 may have an opening 17 for receiving from a line 18 a supply of nitric oxide.

In the illustrated embodiment, a reactor 20 provides a supply of nitric oxide to the distributor 12. As illustrated, one end 22 of a line 18 may connect to the input port 16 of the distributor 12. The opposite end 24 of the line 18 connects to the reactor 20. The opening 26 of the line 18 provides a lumina 26 value or passage 26 for passing the nitric oxide gas from the opening 28 of the fitting 30 on the reservoir 20.

In certain embodiments, the reactor 20 may be manufactured in a single-dose size. Accordingly, the distributor may be reused or disposed of. The reactor 20 may typically be disposed of after a single use. Circumferential hoop stresses are not high. Accordingly, the distributor 12, the line 18, and the reactor 20 may all be fabricated from comparatively lightweight and inexpensive materials such as plastic. Parts may be cast, molded, vacuum formed, assembled from film, or the like.

Figure 2:
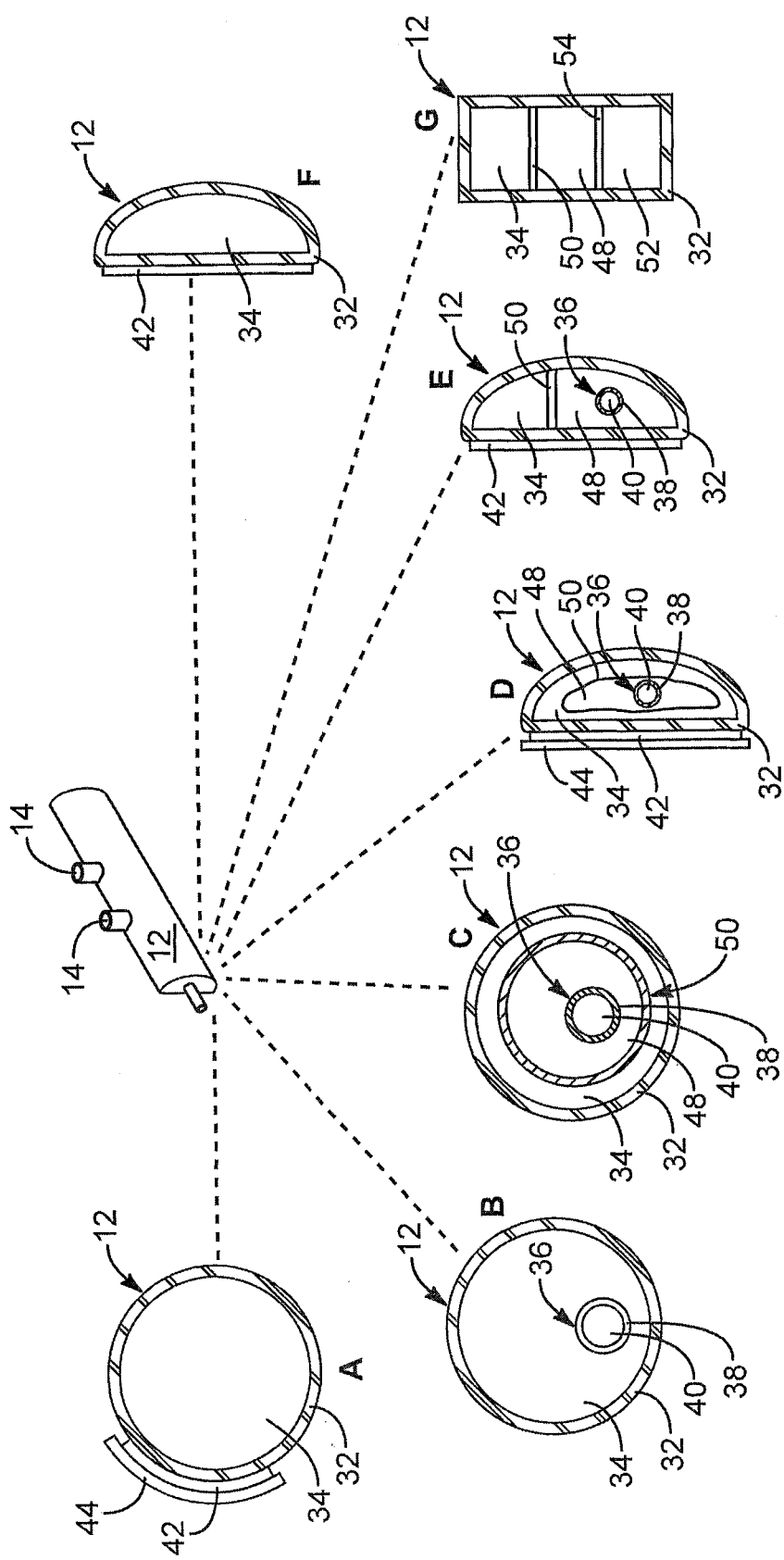
FIG. 2 is an exploded view of alternative, cross-sectional, end views of the distributor of FIG. 1.

Referring to FIG. 2, the distributor 12 may be configured in various cross-sectional shapes. For example, the distributor 12 may typically have a principal wall 32 enclosing a chamber 34 or volume 34 containing the necessary materials for therapy. In certain embodiments, the chamber 34 may simply act as a manifold or distributor channel conducting nitric oxide gas. In other embodiments, the chamber 34 may completely enclose the reaction constituents and structures. Thus, the distributor 12 may serve as both a distributor 12 and reactor 20 in a single, integrated apparatus 10.

In various embodiments, the chamber 34 may include a vessel 36 inside or completely enclosed within the wall 32 and chamber 34 of the distributor 12. The internal vessel 36 may have a wall 38 that is permeable or impermeable. In certain embodiments, the vessel 36 may have a wall 38 formed of glass to maintain the vessel 36 sealed from the contents of the chamber 34. Accordingly, upon fracture of the wall 38, the contents of the vessel 36 may be spilled into the chamber 34 to mix with other reactants.

In certain embodiments, the chamber 40 formed by the wall 38 of the vessel 36 may contain a reactant. In other embodiments, the chamber 40 may simply contain a liquid. In yet other embodiments, the chamber 40 may contain dry ingredients that will become exposed to liquid from the chamber 34 upon fracture of the wall 38 and exposure of the chamber 40 to the contents of the chamber 34. All the foregoing roles can likewise be traded or reversed.

As can be seen, reactants may be separated to render them inactive. The reactants may later be combined to render them active and initiate a reaction. Likewise, the reactants may be maintained in proximity to one another in the chamber 34, the chamber 30, or both, or one may be maintained in a chamber 30, 34 dry and another wet. However, once both reactants are present in the presence of a liquid (e.g., transport fluid) in the opposite chamber 34, 30, the reaction to release nitric oxide may begin.

Any of the embodiments of FIG. 2 may be provided with an adhesive strip 42. One function of the adhesive strip is to secure the distributor 12 proximate the nostrils of a user in order that the distributor 12 may deliver nitric oxide through the openings 15 of the output ports 14. For clarity, the adhesive strip 42 has not been illustrated in every embodiment, although it may. Nevertheless, each of the embodiments may be provided with an adhesive strip 42. Meanwhile, any of the distributors 12 may be secured by some other method.

For example, the distributor 12 may be positioned within a mask covering the nose, the mouth, or both. Likewise, the distributor may be positioned by an air inlet to such a mask. In other embodiments, the distributor 12 may be positioned directly near the mouth, nostrils, or both. Accordingly, the output ports 14 may be shaped to accommodate the positioning thereof for delivery of nitric oxide to the breathing air stream of a subject.

In certain embodiments, an additional volume 48 may be separated within the chamber 34. For example, a layer 50 or wall 50 may seal the reactants away from one another. The wall 50 may be formed of a film, such as a molecular sieve. Such molecular sieves are available from suppliers and may be formed of various materials. One film produced under the trademark Nafion™ operates as a molecular sieve.

The value of a molecular sieve is that it is configured to have a pore size that will not permit passage of a compound of nitrogen having more than a single oxygen. Accordingly, only nitric oxide may pass through the molecular sieve. The molecular sieve, thus restrains the reactant liquids, any particulate matter, and all constituents larger than the nitric oxide molecule. Thus, the nitric oxide molecule may pass through the wall 50 and exit the chamber 34 through the output ports 14.

In yet other embodiments, the basic chamber 34 may be separated away from an additional chamber 48 or volume 48 by a seal 50 or wall 50. Meanwhile, the main chamber 34 may be further subdivided to create an additional volume 52 separated by a wall 54 or seal 54. In the illustrated embodiment, a volume of a first reactant in the chamber 48 is separated entirely from a volume of a second reactant in a chamber 52. Meanwhile, the remaining volume of the chamber 34 may be left as air space to receive the reactant gas passing through the molecular sieve of the layer 50.

Referring to FIG. 2, embodiment A is configured simply as a distributor 12 in which the chamber 34 enclosed by the wall 32 merely passes the nitric oxide for distribution to the output ports 14. Meanwhile, an adhesive layer 42 is bonded to the wall 32 and may be secured to the skin of a user upon removal of a layer 44 or cover 44 protecting the adhesive properties of the layer 42 from their environment during handling.

Embodiment B of FIG. 2 includes an additional chamber 40 separated by a wall 36. In this embodiments, one reactant may occupy the principal chamber 34, while a second reactant occupies the chamber 40 within the wall 36. If the wall 36 is formed of glass, then bending the distributor 12 may fracture the wall 36, exposing the reactants in the chamber 34 to the reactants in the chamber 40. Accordingly, the relative sizes of the chambers 34, 40 may be configured according to the necessary and appropriate quantities of the reactants contained therein, respectively.

The reactants in the chambers 34, 40 may be dry, wet, or one may be dry and one may be wet. Likewise, one chamber 34, 40 may contain both reactive ingredients mixed together but completely dry, while the other chamber 40, 34 contains a liquid capable of acting as a transport medium and thus activating the reaction between the dry ingredients.

Substantially all the illustrated embodiments for a reactor 20 or for a distributor 12 may benefit, as appropriate, from one of the foregoing configurations of dry, wet, or wet and dry ingredients, or dry ingredients and a wet transport material 12.

Embodiment C provides for a distributor 12 having one volume 48 enclosed by a molecular sieve layer 50. Meanwhile, a wall 36 encloses another chamber 40 containing another reactant. In this embodiment, the remainder of the volume of the chamber 34 outside the wall 50 of the molecular sieve is available as free space. Meanwhile, all reactants are contained within the molecular sieve layer 50.

A fracture of the wall 36 may release the reactants from the chambers 40, 48 to mix with one another and react. Meanwhile, the molecular sieve layer 50 contains all the reactants, as well as species of reaction that may be other than nitric oxide. Typically, nitric oxide is the principal output of the proposed reactants. Nevertheless, when exposed to the reaction process too long or when provided with outside oxygen, nitric oxide may become a more oxygenated reactant of nitrogen.

Embodiment D illustrates a more easily bendable shape, that may be more comfortable and more practical for forming about the upper lip of a user. For example, in any illustrated embodiment, any of the materials used to form the wall 32 of the chamber 34 may be comparatively rigid, moderately flexible such as a soft plastic or elastomer, or very flexible such as the materials used to form a toothpaste tube or other collapsible tube for containing a paste or liquid. Accordingly, the distributor 12 may be formed to fit the lip a user. Internal materials such as a wire imbedded in part of the wall 32 may facilitate bending the distributor 12 to a specific and permanent shape. Meanwhile, the adhesive strip 42 may secure a comparatively weak and soft material to the lip of a user and thus maintain the desired shape.

In embodiment D, the molecular sieve layer 50 may be a flexible film that provides additional space in the chamber 34 as gas accumulation space, while still containing the volume 48 of one reactant. In the illustrated embodiment, the chamber 40 is maintained within the wall 38 of a vessel 36. If the vessel 36 has a rigid wall 38, such as one formed of glass, a simple bending of the distributor 12 may permit mixing of the reactants in the chambers 40, 48 and discharge of the nitric oxide reactant through the wall 50 to accumulate in the remaining dry portion of the chamber 34 for ultimate discharge through the output ports 14.

Embodiment E provides a molecular sieve layer 50 permanently disposed across the chamber 34 separating a portion of the chamber 34 from a cavity 48 or volume 48 containing a reactant. Thus, a portion of the chamber 34 remains dry, while a portion is separated off as the volume 48 for containing a reactant. In this embodiment, the volume 40 is likewise contained by a wall 38 as a separate vessel 36 containing one of the reactants. Typical reactants are moderate acids such as citric acid, ascorbic acid, acetic acid, or the like. Meanwhile, typical reactants may involve compositions of nitrogen such as potassium nitrite, sodium nitrite, or the like. Reactants may be disposed as granules, powders, liquids in solution, solutions gelled to thixotropic consistency, or the like.

Embodiment F illustrates a distributor 12 that contains no reactants and does not act as a reactor 20 or reactant chamber 34. Rather, the chamber 34 of embodiment F is simply an empty cavity for distributing nitric oxide to the output ports 14.

Embodiment G may actually be configured in various shapes. However, as a manufacturing matter, alignment, assembly, and the like may be best served by more linear envelopes rather than curved ones. Nevertheless, the arrangement of embodiment G may actually be imposed on other shapes. In this embodiment, the chamber 34 may be separated by a molecular sieve layer 50 from a chamber 48 containing one reactant. Meanwhile, another seal 54 or wall 54 may separate the ingredients in the chamber 48 from the volume 52 or chamber 52 containing the second ingredient.

The entire reaction is contained within the wall 32, but the individual wall 50 acts a molecular sieve and will not be ruptured. By contrast, in order to initiate the reaction, the wall 54 may be compromised by perforating, fracture, rupture, tearing, cutting, or the like. Meanwhile, the remainder of the chamber 34 provides head space for the gas to accumulate for discharge through the output ports 14.

Figure 3:
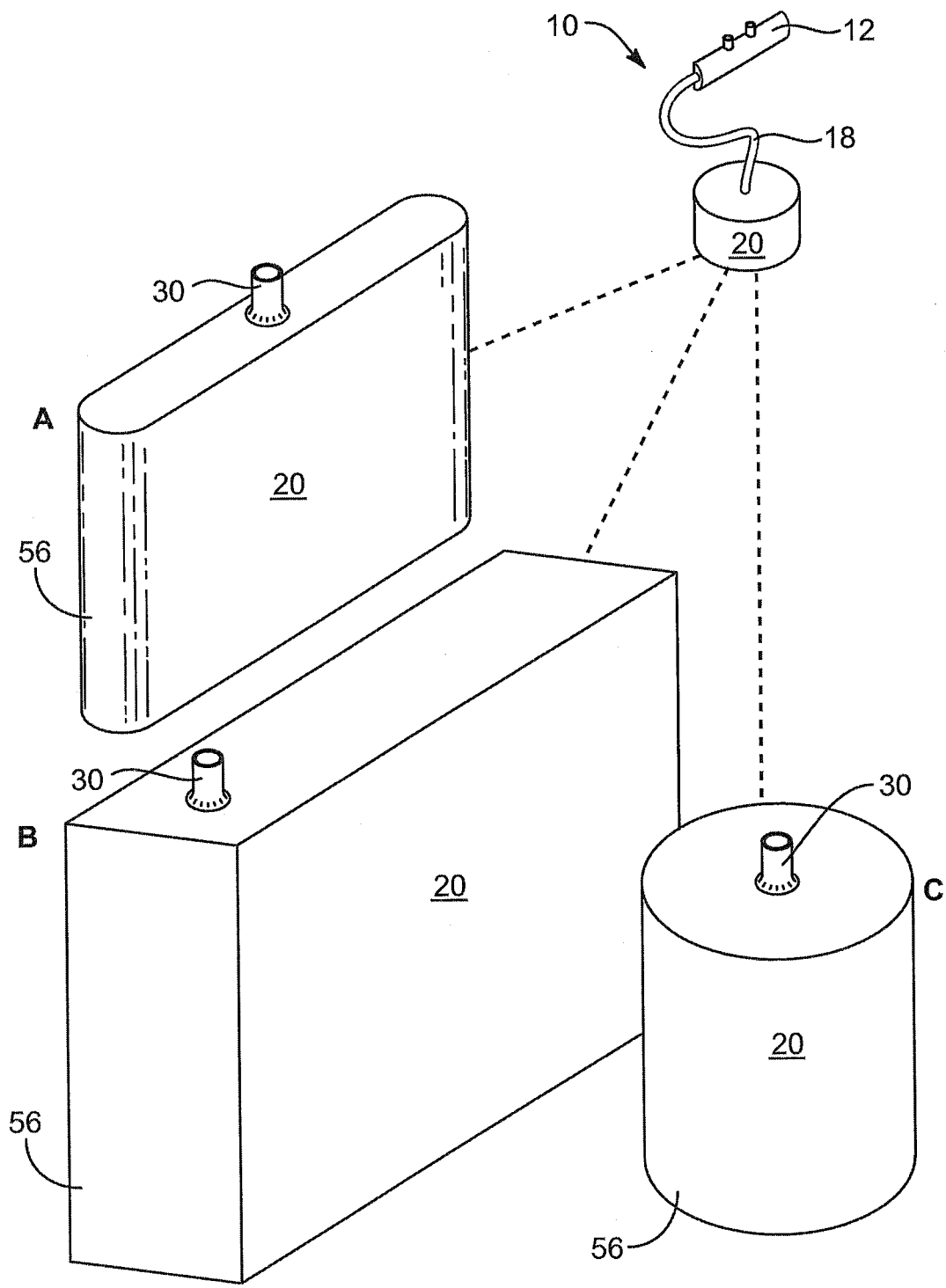
FIG. 3 is a perspective view of various alternative embodiments for a reaction chamber for the apparatus of FIG. 1.

Referring to FIG. 3, a reactor 20 in the apparatus 10 may be configured in any suitable shape. Circular cross-sections tend to provide an equalization of hoop stresses. However, the reaction of materials contemplated for an apparatus 10 in accordance with the invention need not operate at an elevated pressure. Typically, the reaction may occur at about ambient conditions.

In embodiment A of FIG. 3, the reactor 20 may be configured as a rounded, yet somewhat flattened device having an aspect ration of width to thickness that is substantially larger than unity. Thus the width is more than the thickness, and in the illustrated embodiment is several times the thickness. Meanwhile, the aspect ratio of height to width may be selected according to space available in a convenient location for holding the reactor 20. For example, embodiment D may be a suitable configuration for setting on a table top. By contrast, embodiment A may be better suited for slipping into a shirt pocket, jacket pocket, or the like for portability. Meanwhile, the reactor 20 of embodiment C may be suitable for holding in a jacket pocket, or sitting on a night stand beside a bed or other flat surface.

Figure 4:
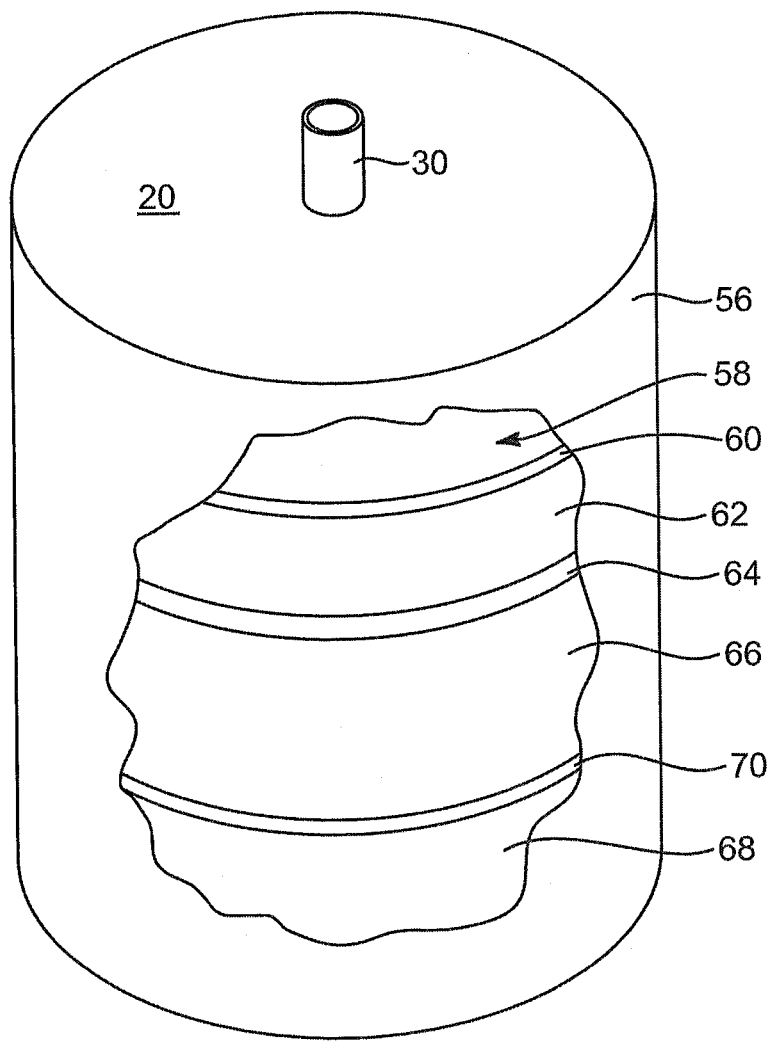
FIG. 4 is a partially cut-away, perspective view of one embodiment of a reactor for use in the apparatus of FIGS. 1-3.

Referring to FIG. 4, any of the reactors 20 of FIG. 3 may be configured to contain any or all of the chambers of FIG. 2. The reactor 20 may enclose various individual volumes. For example, in the illustrated embodiment, a volume 58 is enclosed within the wall 56 of the reactor 20. The volume 58 is bounded below by a layer 60 or sieve layer 60.

Optionally, a region of expansion space 62 may exist above a closure layer 64. The layer 64 initially forms a retainer or seal 64 to contain the volume 66 of a first reactant. The first reactant volume 66 is separated from a volume 68 containing the second reactant by a seal 70 that may be ruptured or otherwise compromised to initiate a reaction.

The closure layer 64 may be permeable. Alternatively it may be sealed impervious, to be breached in preparation for initiating the reaction in the reactor 20. It may be burst or otherwise opened or by the reaction.

In one embodiment, the layers 64, 70 may be formed of a polymer film, wax, or the like capable of maintaining the volumes 66, 68 separated from one another with their reactants. A mechanism such as a plunger, perforator, mixer, spatula, or other apparatus extending through the wall 56 may serve to break, rupture, tear, cut, or otherwise compromise the layer 70. Likewise, the layer 64 may be so opened and compromised in order to make the expansion space 62 available to the reactants.

The reactants in the volumes 66, 68 may be solid, liquid, one of each, or some other combination. For example, an additional layer, possibly even including the volume 62, may contain a liquid to provide a transport fluid for dry reactants in the volume surface 66, 68.

By whatever mechanism, the layers 64, 70 may be opened to expose the volumes 66, 68 with their reactant contents to one another in order to activate the reactor 20 and begin the chemical reaction to produce nitric oxide. Nitric oxide passes through the molecular sieve layer 60, which may be optional, but is useful in maintaining the purity of nitric oxide. The molecular sieve 60 or the layer 60 may include not only a molecular sieve, such as a film or solid layer, but may also include any other barrier materials suitable to maintain reactants outside of the collection volume 58 collecting the nitric oxide.

Ultimately, the nitric oxide in the volume 58 is passed through the fitting 30 into a line 18 for delivery into a distributor 12. Notwithstanding the illustrated embodiment of FIG. 4, any suitable shape may be used for the cross-section of the reactor 20. Accordingly, the reactor of FIG. 4 may actually be configured according to the relations, shapes, or both illustrated in any of the alternative embodiments illustrated in FIGS. 1-3.

In one alternative embodiment, the wall 56 may be highly flexible. Moreover, shape may be selected having an aspect ration of length to width that is comparatively larger than unity. The ratio of width to thickness may also be selected to be substantially larger than unity. Accordingly, the reactor 20 may be configured as a comparatively long, narrow tube, of a comparatively smaller thickness. Accordingly, the reactor 20 may be rolled up like a toothpaste tube or kneaded in order to rupture the seal layers 64, 70 and to mix the reactants in the volumes 66, 68.

If the volumes 66, 68 are filled with solutions, for example, reactants disposed in a solute liquid, or freely flowing gel, then mixing may readily occur. In other embodiments, diffusion alone may control the migration of reactant species between the volumes 66, 68. Thus, sealing layers 64, 70 may be formed, dividing the chambers or volumes 66, 68 containing reactants, which may then be extruded, mixed, drawn, flown, stirred, or otherwise introduced to one another to increase the available species participating in the reaction.

Figure 5:
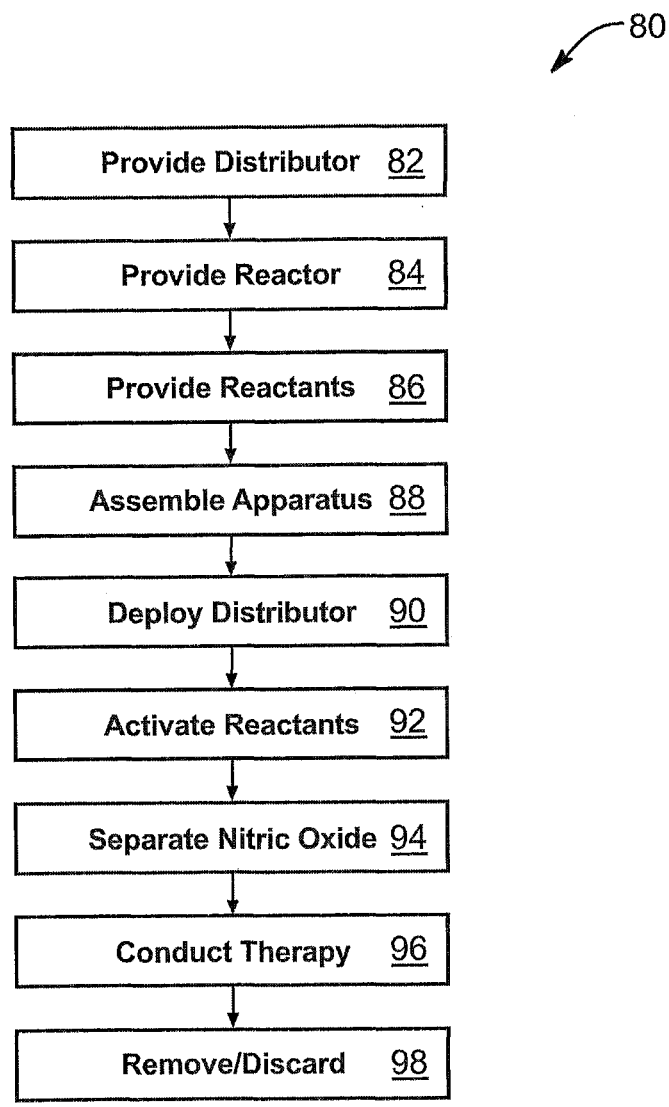
FIG. 5 is a schematic block diagram of one embodiment of a method in accordance with the invention.

Referring to FIG. 5, one embodiment of an apparatus and method in accordance with the invention may rely on a series of process steps constituting a method 80 or process 80. For example, providing 82 a distributor 12 may involve any one or more of the required tasks of identifying materials, selecting a shape, selecting a cross-sectional profile and area, selecting aspect ratios of length to width to thickness, and determining the structural and mechanical characteristics for such a distributor 12. Accordingly, providing a distributor 12 may involve design, engineering, manufacture and acquisition of such a device.

Providing 80 a reactor may involve selection of materials, selection profile and of cross-sectional area, engineering, design, fabrication, acquisition, purchase, or the like of a reactor 20 in accordance with the discussion hereinabove.

Providing reactants 86 may include selection of reacting species, selecting a configuration, such as granules, powder, liquid, a solution, or the like. Likewise, the particular configuration of a solidous configuration of reactants may involve selecting a sieve size for the particles. This site can affect chemical reaction rates. Thus, selecting or otherwise providing 86 reactants for the reactor 20 may involve consideration of any or all aspects of chemistry, reaction kinetics, engineering, design, fabrication, purchase or other acquisition, delivery, assembly, or the like.

Assembling 88 the apparatus may involve a single distributor as an integrated embodiment as described with respect to FIG. 2, or assembly of a reactor, with a feed line 18, connected to a distributor 12. Likewise, assembling 88 may also include the disposition of reactants within various locations within a reactor 20, distributor 12, or the like as discussed hereinabove.

Deploying 90 the distributor may involve opening up a package provided during assembly 88 of the apparatus 10. For example, assembling 88 may also include packaging. Accordingly, deploying 90 may involve opening packages, unsealing components, and otherwise rendering the apparatus 10 ready for use. Likewise, deploying 90 the distributor 12 may involve positioning the distributor 12 with respect to a user, including, for example, adhering the distributor 12 to the skin of a user proximate the nostrils for inhaling the nitric oxide provided by the distributor 12.

Activating 92 the reactants in the reactor 20 may involve, either adding a liquid, mixing the reactant components together, dispersing individual reactants in respective solutes to provide solutions for mixing, adding a liquid transport carrier to dry ingredients in order to initiate exchange between reactants, a combination thereof, or the like.

Likewise, activation 92 of the reactants may also involve opening valves, opening seals, rupturing or otherwise compromising seals as described hereinabove, or otherwise moving or manipulating reactants with or without carriers in order to place them in chemical contact with one another.

In certain embodiments, nitric oxide may be separated 94 from the reactants themselves. For example, the concept of a molecular sieve 60 was introduced hereinabove as one mechanism to separate 94 nitric oxide form other reactants and from other species of nitrogen compounds. In other embodiments, pumps, vacuum devices, or the like may also tend to separate 94 nitric oxide. Accordingly, in certain embodiments, a suitably sized pump may actually be connected to the reactor 20 in order to draw nitric oxide away from other species of reactants or reacted outputs.

Conducting 96 therapy using nitric oxide may involve a number of steps associated with delivery and monitoring of nitric oxide through the distributor 12. For example, in certain embodiments, conducting 96 therapy may involve activating a reactor 20 or the contents thereof. Likewise, conducting 96 a therapy session may involve proper application of the distributor 12 to the person of the user such as by adhering an adhesive strip 42 to the skin of a user in order to position the output ports 14 in the nostrils of a user for receiving nitric oxide therefrom. It may include assembling the necessary conduit 18 or line 18 with the distributor 12 to send nitric oxide from the reactor 20 to the distributor 12, and ultimately to a user.

Monitoring may involve adding gauges or meters, taking samples, or the like in order to verify that the delivery of nitric oxide from the reactor 20 to the distributor 12 does meet the therapeutically designed maximum and minimum threshold requirements specified by a medical professional.

Ultimately, after the expiration of an appropriate time specified, or the exhaustion of a content of a reactor 20, a therapy session may be considered completed. Accordingly, the apparatus 10 may be removed 98 from use, discarded, or the like. Accordingly, the removal or discarding 98 of the apparatus 10 may be by parts, or by the entirety. For example, the distributor 12, if it does not include an integrated reactor therewithin, may simply act as a manifold and be reused with a new reactor 20.

It is contemplated that the reactor 20 may typically be a single dose reactor but need not be limited to such. Multiple-dose or reusable reactors may also be used. For example, the reactor 20 may actually contain a cartridge placed within the wall 56. The internal structure of the cartridge may be ruptured in the appropriate seal locations, such as the seals 64, 70 by a mechanism associated with the main containment vessel or wall 56, and thus activated. Accordingly, the reactor 20 may be reused by simply replacing the cartridge of materials containing the reactant volumes 66, 68.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for nitric oxide therapy comprising:
   providing a distributor placed to deliver nitric oxide to a breathing stream of a user;
   providing a reactor producing nitric oxide wherein the reactor is portable with the user and sized to contain reactants sufficient to provide a single therapy session dose of nitric oxide and is connected in fluid communication with the distributor, wherein the reactor contains at least two reactants comprising a first reactant contained in a first chamber and a second reactant contained in a second chamber, the reactants being separated by a chamber wall that is ruptured to promote mixing;

initiating production of nitric oxide by mixing reactants in the reactor;

separating the nitric oxide from reactants and other species resulting from the reaction by filtering the nitric oxide through a porous molecular sieve that contacts one of the first or second reactants; and delivering the nitric oxide to the distributor.

2. The method of claim 1, further comprising providing a securement to secure the distributor on the person of the user after providing the reactor.

3. The method of claim 2, wherein the distributor is positioned and secured to deliver the nitric oxide directly into the nostrils of the user.

4. The method of claim 2, wherein the securement includes an adhesive strip securing the distributor to the user.

5. The method of claim 1, wherein the concentration of nitric oxide delivered from the distributor to the user is from about one thousand parts per million to about ten thousand parts per million of nitric oxide.

6. The method of claim 1, wherein at least a portion of the second chamber is contained within the first chamber.

7. The method of claim 1, wherein the reactor is non-toxic after use.

8. The method of claim 1, wherein the first reactant is a composition of nitrogen and the second reactant is a moderate acid.

9. The method of claim 8, wherein the first reactant comprises at least one composition of nitrogen selected from the group consisting of potassium nitrite and sodium nitrite and the second reactant comprises at least two moderate acids selected from the group consisting of citric acid, ascorbic acid, and acetic acid.

10. A method for nitric oxide therapy comprising:

providing a distributor placed to deliver nitric oxide directly into the nostrils of a user;

providing a reactor comprising at least a first chamber and a second chamber wherein the first chamber contains at least one composition of nitrogen selected from the group consisting of potassium nitrite and sodium nitrite and the second chamber contains at least two moderate acids selected from the group consisting of citric acid, ascorbic acid, and acetic acid and the first and second chambers separated by a rupturable chamber wall;

the providing the reactor further comprising providing the reactor sized to be portable and connected in fluid communication with the distributor;

the providing a reactor further comprising providing a single therapy session dose of nitric oxide to the user;

initiating production of nitric oxide by mixing the reactants in the first and second chambers;

separating the nitric oxide from the reactants and other species resulting from the reaction by filtering the nitric oxide through a porous molecular sieve that contacts one of the first or second reactants; and delivering through the distributor to the user a concentration of nitric oxide from about one thousand parts per million to about ten thousand parts per million of nitric oxide.

\* \* \* \* \*